United States Patent [19]
Ollar

[11] Patent Number: 5,776,722
[45] Date of Patent: Jul. 7, 1998

[54] METHOD OF TESTING A BODY SPECIMEN TAKEN FROM A PATIENT FOR THE PRESENCE OR ABSENCE OF A MICROORGANISM A FURTHER ASSOCIATED METHOD AND ASSOCIATED APPARATUS

[75] Inventor: Robert A. Ollar, Milford, Pa.

[73] Assignee: Infectech, Inc., Sharon, Pa.

[21] Appl. No.: 936,924

[22] Filed: Sep. 25, 1997

[51] Int. Cl.$^6$ .................. C12Q 1/02; C12Q 1/00; C12Q 1/04; C12Q 1/14
[52] U.S. Cl. .................. 435/29; 435/4; 435/975; 435/34; 435/36; 435/252.1; 435/288.1; 435/287.3
[58] Field of Search .................. 435/29, 4, 975, 435/34, 36, 252.1, 288.1, 287.3

[56] References Cited

U.S. PATENT DOCUMENTS

| | | | |
|---|---|---|---|
| 5,153,119 | 10/1992 | Ollar | 435/34 |
| 5,316,918 | 5/1994 | Ollar | 435/34 |
| 5,472,877 | 12/1995 | Ollar | 435/288.1 |
| 5,569,592 | 10/1996 | Ollar | 435/32 |
| 5,637,501 | 6/1997 | Ollar et al. | 435/286.2 |
| 5,639,675 | 6/1997 | Felder et al. | 435/29 |
| 5,641,645 | 6/1997 | Felder et al. | 435/32 |
| 5,654,194 | 8/1997 | Felder et al. | 435/287.9 |
| 5,663,056 | 9/1997 | Ollar et al. | 435/29 |
| 5,668,010 | 9/1997 | Felder et al. | 435/287.9 |
| 5,677,169 | 10/1997 | Ollar et al. | 435/287.9 |

*Primary Examiner*—Louise N. Leary
*Attorney, Agent, or Firm*—David V. Radack; Eckert Seamans Cherin & Mellott, LLC

[57] ABSTRACT

A method of testing a body specimen taken from a patient for the presence or absence of a microorganism. A transport/isolator assembly is provided which includes a receptacle and a baiting assembly including a baiting section having disposed thereon a coating material. A baiting liquid and the body specimen are then introduced into the receptacle. The method further comprises securing the baiting assembly to the receptacle so that at least a portion of the coated section is introduced into the baiting liquid. The transport/isolator assembly containing the baiting liquid and the body specimen are then transported to a laboratory for subsequent observation of the coated section for growth or lack thereof of the microorganism. A further method of processing the body specimen and an associated isolator/transport assembly kit as well as an associated isolator/transport assembly are also disclosed.

40 Claims, 2 Drawing Sheets

METHOD OF TESTING A BODY SPECIMEN TAKEN FROM A PATIENT FOR THE PRESENCE OR ABSENCE OF A MICROORGANISM A FURTHER ASSOCIATED METHOD AND ASSOCIATED APPARATUS

BACKGROUND OF THE INVENTION

This invention relates to a method of testing a body specimen taken from a patient for the presence or absence of a microorganism. An associated method of processing the body specimen and an associated isolator/transport assembly kit as well as an associated isolator/transport assembly are also disclosed.

Several of my United States Patents teach a practical, economic method of determining the presence or absence of both paraffinophilic microorganisms and nonparaffinophilic microorganisms. The method involves providing a receptacle and placing into the receptacle a liquid media, such as Czapek broth, and then introducing into the receptacle a body specimen taken from a patient. After this, a slide coated with paraffin (for paraffinophilic microorganisms) or a carbon source (for nonparaffinophilic microorganisms) is placed into the receptacle. Subsequent observation/analysis of the growth or lack thereof on the slide will enable determination of the presence or absence of either a paraffinophilic microorganism or a nonparaffinophilic microorganism in the body specimen.

In some situations, obtaining the body specimen and introducing it into the receptacle will occur at a different place than the observation of the growth. Furthermore, there may be an incubation period necessary for the growth to occur. For example, the body specimen may be taken from the patient and introduced into the receptacle at a doctor's office and then must be transported to a laboratory for further observation/analysis.

What is needed, therefore, is an economical, efficient and effective method and apparatus for transporting and isolating the microorganism in a receptacle.

SUMMARY OF THE INVENTION

The invention has met or exceeded the above-mentioned needs as well as others. The method of the invention involves testing a body specimen taken from a patient for the presence or absence of a microorganism. The method comprises providing a transport/isolator assembly including (i) a receptacle and (ii) a baiting assembly including a baiting section having disposed thereon a coating material. A baiting liquid and the body specimen are then introduced into the receptacle. The method further comprises securing the baiting assembly to the receptacle so that at least a portion of the baiting section is introduced into the baiting liquid. The transport/isolator assembly containing the baiting liquid and the body specimen are then transported to a laboratory for subsequent observation of the baiting section for growth or lack thereof of the microorganism.

A method of processing a body specimen for subsequent analysis to determine the presence or absence of a microorganism in a body specimen is also provided. This method includes providing a transport/isolator assembly including (i) a receptacle and (ii) a baiting assembly including a baiting section having disposed thereon a coating material. A baiting liquid and the body specimen are then introduced into the receptacle. The method further comprises securing the baiting assembly to the receptacle so that at least a portion of the baiting section is introduced into the baiting liquid.

A transport/isolator assembly kit is also provided. The transport/isolator assembly comprises a receptacle, a baiting assembly including a baiting section having disposed thereon a coating material and a liquid media for introduction into the receptacle. The baiting assembly is adapted to be mechanically secured to the receptacle.

A transport/isolator assembly is further provided which includes the receptacle and the baiting assembly.

BRIEF DESCRIPTION OF THE DRAWINGS

A full understanding of the invention can be gained from the following detailed description of the invention when read in conjunction with the accompanying drawings in which.

DETAILED DESCRIPTION

Figure 1:
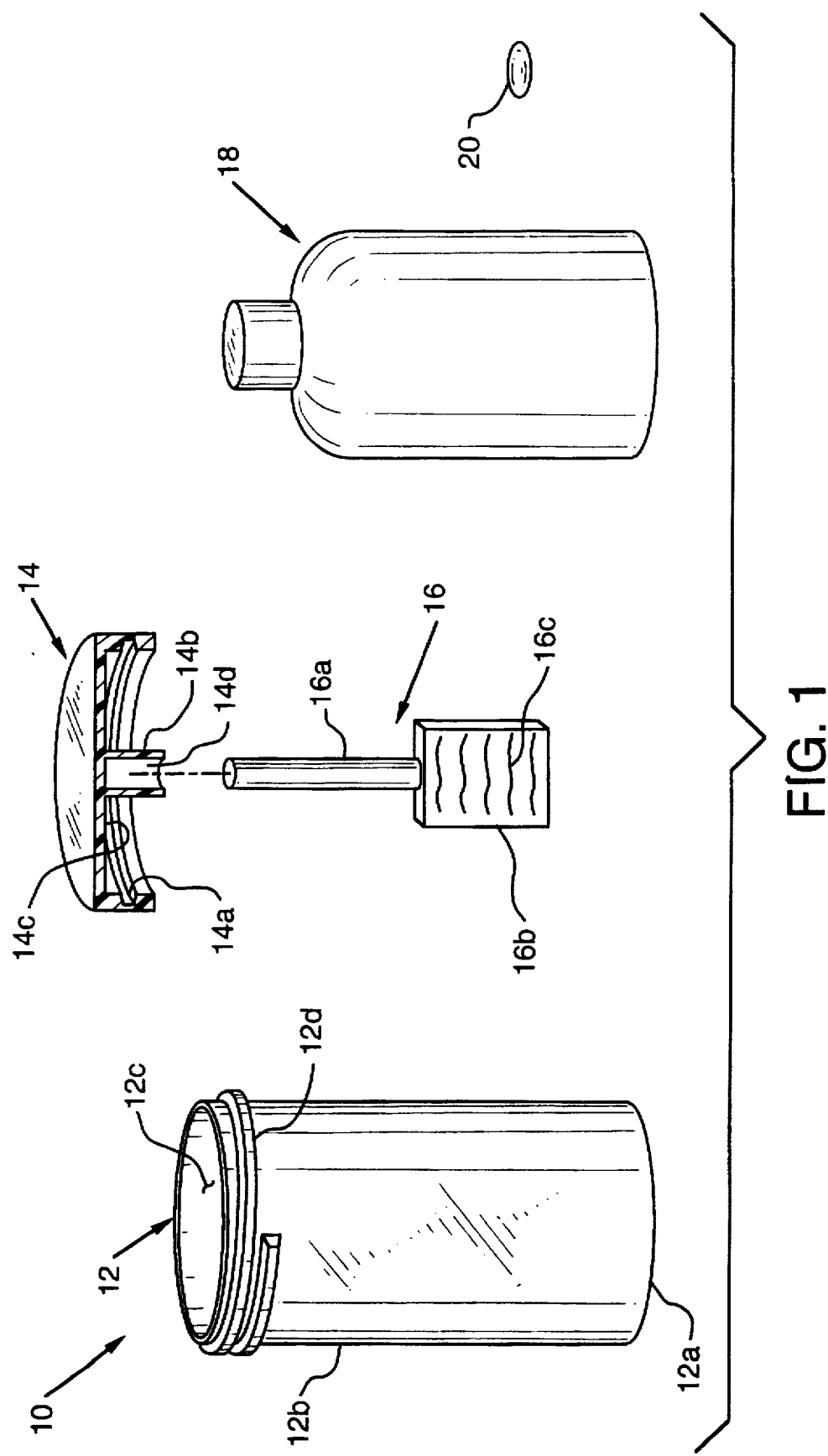
FIG. 1 is a perspective view, having some partially sectioned portions of the transport/isolator kit assembly showing the separate parts of the kit.

Referring now to FIG. 1, the kit 10 of the invention is shown. The kit 10 includes a receptacle 12, preferably made of polystyrene plastic, which is cylindrical in cross-section and which preferably has a flat bottom 12a so that it can rest on a flat surface without the need for a separate stand. The receptacle 12 can have a capacity of from about 10–500 ml. One preferable receptacle has a capacity of between about 10–20 ml, a height of about 8–10 cm and a diameter of about 2.5–3.0 cm. It will be further appreciated that the top 12b of the receptacle defines a circular opening 12c, and that the top 12b of the receptacle has disposed thereon male threads 12d, whose purpose will be discussed below. The receptacle can be made of other materials, such as glass, and can have other shapes and sizes than that illustrated in FIG. 1, so long as the general purpose of the receptacle is maintained, in accordance with the invention.

The kit 10 further includes a cap member 14. The cap member 14 is also preferably made of plastic and includes female threads 14a which are complementary to male threads 12d so that cap member 14 may securely and threadedly engage the receptacle. It will be appreciated that other methods of securing the cap 14 to the receptacle 12 can be used, such as by a friction-fitting cap or by securing the cap 14 to the receptacle by adhesives. The cap member 14 shown in FIG. 1 also includes a cylindrical cuff portion 14b (shown in partially cutaway section) which extends downwardly from the underside 14c of the cap member 14. The cuff portion 14b defines a cuff member opening 14d having a circular cross-section whose purpose will be discussed below.

A baiting assembly 16 is next provided. The baiting assembly 16 comprises a connecting portion 16a and a baiting section, shown in FIG. 1 in the form of a paddle 16b. The connecting portion 16a is preferably made of plastic whereas the paddle 16b is preferably made of glass. The size and shape of the baiting assembly either dictates or is dictated by the size and shape of the receptacle 12. It is preferred, however, that the size of the baiting assembly 16 be such that when assembled (FIG. 2) the baiting assembly is suspended in the receptacle so that (i) the paddle 16b is submerged in the liquid and (ii) the paddle 16b does not touch the bottom 12a of the receptacle 12. In this way, it will be assured that the paraffinophilic microorganism (if present in the specimen) will attach and grow efficiently and effectively on the paddle 16b.

The top section 16c of the connecting portion 16a is adapted to be friction fit into the cuff member opening 14d of the cap member 14 in order to removably secure the baiting assembly 16 to the cap member 14. It will be appreciated that other removable securement methods, such as threads or clips can be used. The baiting assembly 16 is preferably removably secured to the cap member 14 in order to enable reuse of the cap member 14 with either baiting assemblies, however, if desired, the cap member 14 and baiting assembly 16 can be constructed as an integral unit.

Figure 2:
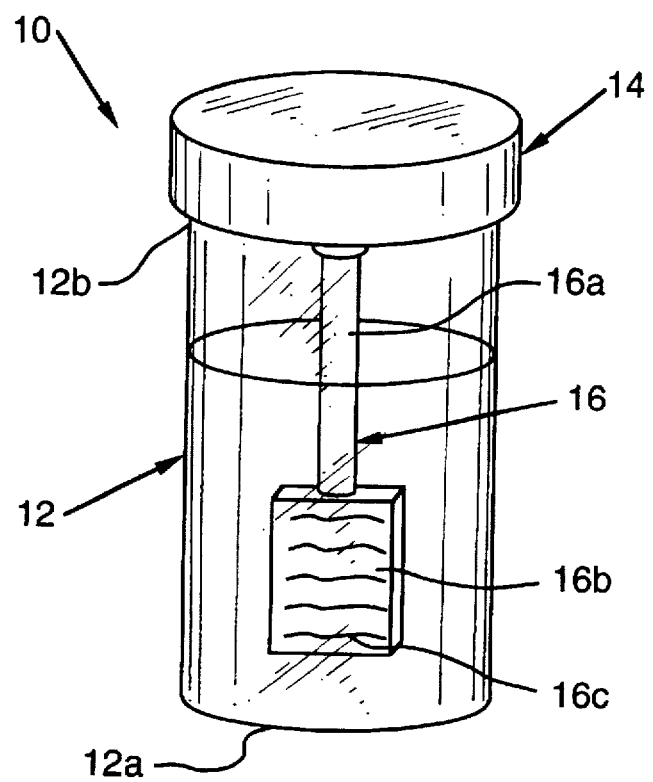
FIG. 2 is a perspective view showing the assembled transport/isolator assembly.

The paddle 16b of the baiting assembly 16 is coated with a coating material. FIGS. 1 and 2 show a paraffin wax 16c as the coating material, as this kit 10 will be used to detect paraffinophilic microorganisms. As used herein, the term "paraffinophilic" means an organism that can employ paraffin wax as a source of carbon in a basal salt media, devoid of other forms of carbon. The organism can be bacterial or fungal in nature. Examples of paraffinophilic microorganisms are *Micrococcus Paraffinae; Corynebacterium Simplex; Abnl; Mycococcus (Rhodococcus) Cinnabareus; Ahnl. Mycococcus (Rhodoc) Rhodochrous; Mycobact. Perrugosum Var. Athanicum; Mycobact. Rubrum Var. Propanicum; Mycobacterium Hyalinum; Mycobacterium Lacticola; Mycobacterium Album, M. Luteum; Mycobacterium Microti; Mycobacterium Rubrum, Mycobacterium Phlei.; Mycobacterium Phlei, M. Smegmatis; Mycobacterium Testudo; Mycobacterium-Avium-Intracellulare; Nocardia Spp.; Actinomyces; Candida Lipolytica; Candida Tropicalis, Torulopsis Colliculosa; Monila Sp., Hansenula Sp., Torula rossa; Penicillium Sp.; IHNL. Aspergillus Flavus; Aspergillus sp., Penicillium Sp.; Citromyces Sp., Scopulariopsis Sp.; Pseudomonas Fluorescens Liquefaciens; Ahnl, Pem. Fluorescens Denitrificans; Pseudomonas Aeruginosa.*

It will also be appreciated that, in accordance with the invention, a kit is also provided that can be used to determine the presence or absence of nonparaffinophilic microorganisms. As used herein, the term "nonparaffinophilic" means any microorganism sustained by a carbon source other than paraffin. Examples of such nonparaffinophilic microorganisms include, but are not limited to the following: *Mycobacterium tuberculosis; Mycobacterium paratuberculosis; Mycobacterium leprae;* Staphylococcus; Streptococcus; *E. coli;* Listeria; Brucellae; Humemophilus; Treponema; Pneumococcus; Clostridium; Cryptococcus; Coccidioides; and Histoplasma. In this case, the coating material on the paddle 16b is a gelatinous matrix containing a carbon source other than paraffin and can be one or more of those selected from the group consisting of glucose, fructose, glycerol, mannitol, asparagine, urea, casein and hydrolyzate, among others. Another coating material can include coating the slide with an adhesive and securing a plurality of gel beads to the adhesive. The carbon source can then be either ionically or affinity bound to the gel beads. For a more detailed description of the coating, reference is made to commonly owned U.S. patent application Ser. No. 08/528,189 filed Sep. 14, 1995, the disclosure of which is incorporated by reference herein.

Also, the coating material can be a hydrophobic material, which can be used for hydrophobic baiting of the microorganism. Examples of hydrophobic materials are plastic or silicone.

The kit 10 further includes a vial 18 of baiting liquid, such as Czapek broth, which is poured into the receptacle when the kit 10 is used, as will be explained below. The amount of baiting liquid provided will be dictated by the size of the receptacle 12, however, it is preferred that when the baiting liquid and the specimen (not shown) are placed into the receptacle 12, that the liquid level in the receptacle be such that the paddle 16b of the baiting assembly 16 is submerged. A typical amount is 5–15 ml. The kit 10 also includes a dehydrated antibiotic cocktail 20, such as PANTA-PLUS™ made by the Becton Dickinson Company. This cocktail 20 will be used when the specimen, such as fecal matter, may contain other virulent bacteria that must be killed. The PANTA-PLUS™ can also be provided in a liquid form, in a separate vial.

FIG. 2 shows the transport/isolator assembly in an assembled form. It will be appreciated that the specimen (not shown) has already been added into the receptacle 12. The specimen can be blood, fecal matter, sputum, gastrointestinal fluid, cerebrospinal fluid or any of many numerous body specimens that are desired to be analyzed for the presence of microorganisms.

The following example will describe the operation of the methods of the invention.

EXAMPLE

An AIDS patient comes to a doctor's office or other medical facility such as a hospital, complaining of severe abdominal pain. A gastroenterologist uses a gastrointestinal scope to obtain a specimen of the patient's stomach fluid. This specimen is introduced into a receptacle 12 already having therein a baiting liquid, such as Czapek broth 18. The baiting assembly 16, consisting of the threaded cap 14, the connecting portion 16a and the paraffin coated slide paddle 16b are then placed into the receptacle, with the cap being screwed onto the receptacle. The receptacle, including the secured baiting assembly, the baiting liquid and the body specimen, is then transported to a laboratory. After a period of time, growth is detected on the slide and it is determined that this growth is Mycobacterium-Avium-Intracellulare ("MAI")

It will be appreciated that a transport/isolator assembly kit and associated methods are provided whereby medical personnel can obtain, quickly and easily, an identification of a microorganism in a body specimen.

While specific embodiments of the invention have been disclosed, it will be appreciated by those skilled in the art that various modifications and alterations to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. A method of testing a body specimen taken from a patient for the presence or absence of a microorganism, said method comprising;

providing a transport/isolator assembly including (i) a receptacle and (ii) a baiting assembly including a baiting section having disposed thereon a coating material;

introducing a baiting liquid into said receptacle;

introducing said body specimen into said receptacle;

securing said baiting assembly to said receptacle so that at least a portion of said baiting section is introduced into said baiting liquid;

transporting said transport/isolator assembly containing said baiting liquid and said body specimen to a laboratory; and observing said baiting section at said laboratory for growth or lack thereof of said microorganism.

2. The method of claim 1, wherein said microorganism is a paraffinophilic microorganism and said coating material is paraffin wax.

3. The method of claim 1, wherein said microorganism is a nonparaffinophilic microorganism and said coating material is a carbon source selected from the group consisting of glucose, fructose, glycerol, mannitol, asparagine, urea, casein and hydrolyzate.

4. The method of claim 1, wherein said microorganism is a nonparaffinophilic microorganism; and said coating material includes (i) an adhesive disposed on said baiting section; (ii) a plurality of gel beads secured to said adhesive; and (iii) a carbon source which is either ionically or affinity bound to said gel beads.

5. The method of claim 1, wherein said coating material is a hydrophobic material.

6. The method of claim 5, wherein said hydrophobic material is selected from the group consisting of plastic and silicone.

7. The method of claim 1, including obtaining said body specimen at a medical facility; and introducing said baiting liquid and said body specimen into said receptacle at said medical facility shortly after obtaining said body specimen from said patient.

8. The method of claim 7, wherein said medical facility is a doctor's office.

9. The method of claim 1, wherein said baiting liquid contains an antibiotic cocktail.

10. The method of claim 1, wherein said body specimen is selected from the group consisting of blood, fecal matter, sputum, gastrointestinal fluid and cerebrospinal fluid.

11. A method of processing a body specimen for subsequent analysis to determine the presence or absence of a microorganism in said body specimen, said method comprising:

providing a transport/isolator assembly including (i) a receptacle and (ii) a baiting assembly including a baiting section having disposed thereon a coating material;

introducing a baiting liquid into said receptacle;

introducing said body specimen into said receptacle; and securing said baiting assembly to said receptacle so that at least a portion of said baiting section is introduced into said baiting liquid.

12. The method of claim 11, wherein said microorganism is a paraffinophilic microorganism and said coating material is paraffin wax.

13. The method of claim 11, wherein said microorganism is a nonparaffinophilic microorganism and said coating material is a carbon source selected from the group consisting of glucose, fructose, glycerol, mannitol, asparagine, urea, casein and hydrolyzate.

14. The method of claim 11, wherein said microorganism is a nonparaffinophilic microorganism; and said coating material includes (i) an adhesive disposed on said baiting section; (ii) a plurality of gel beads secured to said adhesive; and (iii) a carbon source which is either ionically or affinity bound to said gel beads.

15. The method of claim 11, wherein said coating material is a hydrophobic material.

16. The method of claim 15, wherein said hydrophobic material is selected from the group consisting of plastic and silicone.

17. The method of claim 11, including obtaining said body specimen at a medical facility; and introducing said baiting liquid and said body specimen into said receptacle at said medical facility shortly after obtaining said body specimen from said patient.

18. The method of claim 17, wherein said medical facility is a doctor's office.

19. The method of claim 11, wherein said baiting liquid contains antibiotic cocktail.

20. The method of claim 11, wherein said body specimen is selected from the group consisting of blood, fecal matter, sputum, gastrointestinal fluid and cerebrospinal fluid.

21. A transport/isolator assembly kit comprising:

a receptacle;

a baiting assembly including a baiting section having disposed thereon a coating material, said baiting assembly adapted to be mechanically secured to said receptacle; and a liquid media for introduction into said receptacle.

22. The kit of claim 21, wherein said liquid media includes an antibiotic cocktail.

23. The kit of claim 22, wherein said liquid media is Czapek broth.

24. The kit of claim 21, wherein said baiting assembly further includes a receptacle engaging means for mechanically securing said baiting assembly to said receptacle.

25. The kit of claim 24, wherein said receptacle engaging means includes a threaded cap portion which engages a complementary threaded portion disposed on said receptacle.

26. The kit of claim 25, including a connecting portion having a first end removably secured to said threaded cap portion and a second end secured to said baiting section.

27. The kit of claim 21, wherein said coating material is paraffin wax.

28. The kit of claim 21, wherein said coating material is a carbon source selected from the group consisting of glucose, fructose, glycerol, mannitol, asparagine, urea, casein and hydrolyzate.

29. The kit of claim 21, wherein said coating material includes (i) an adhesive disposed on said baiting section; (ii) a plurality of gel beads secured to said adhesive; and (iii) a carbon source which is either ionically or affinity bound to said gel beads.

30. The kit of claim 21, wherein said coating material is a hydrophobic material.

31. The kit of claim 30, wherein said hydrophobic material is selected from the group consisting of plastic and silicone.

32. A transport/isolator assembly comprising:

a receptacle; and a baiting assembly including a baiting section having disposed thereon a coating material, said baiting assembly adapted to be secured to said receptacle.

33. The assembly of claim 32, wherein said baiting assembly includes a receptacle engaging means for mechanically securing said baiting assembly to said receptacle.

34. The assembly of claim 33, wherein said receptacle engaging means includes a threaded cap portion which engages a complementary threaded end portion on said receptacle.

35. The assembly of claim 34, wherein a connecting portion having a first end secured to said cap and a second end secured to said coated section.

36. The assembly of claim 32, wherein said coating material is paraffin wax.

37. The assembly of claim 32, wherein said coating material is a carbon source selected from the group consisting of glucose, fructose, glycerol, mannitol, asparagine, urea, casein and hydrolyzate.

38. The assembly of claim 32, wherein said coating material includes (i) an adhesive disposed on said baiting section; (ii) a plurality of gel beads secured to said adhesive; and (iii) a carbon source which is either ionically or affinity bound to said gel beads.

39. The assembly of claim 32, wherein said coating material is a hydrophobic material.

40. The assembly of claim 39, wherein said hydrophobic material is selected from the group consisting of plastic and silicone.

* * * * *

UNITED STATES PATENT AND TRADEMARK OFFICE
CERTIFICATE OF CORRECTION

PATENT NO. : 5,776,722
DATED : July 7, 1998
INVENTOR(S) : ROBERT A. OLLAR It is certified that error appears in the above-identified patent and that said Letters Patent is hereby corrected as shown below:

Column 3, line 20, "Abn1" should be --Ahn1--.

Signed and Sealed this

Sixth Day of July, 1999

*Attest:*

Q. TODD DICKINSON

*Attesting Officer*  Acting Commissioner of Patents and Trademarks